(12) United States Patent
Hicks

(10) Patent No.: US 8,267,884 B1
(45) Date of Patent: Sep. 18, 2012

(54) WOUND TREATMENT APPARATUS AND METHOD

(75) Inventor: Robert F. Hicks, Los Angeles, CA (US)

(73) Assignee: Surfx Technologies LLC, Culver City, CA (US)

( * ) Notice: Subject to any disclaimer, the term of this patent is extended or adjusted under 35 U.S.C. 154(b) by 1007 days.

(21) Appl. No.: 11/539,784

(22) Filed: Oct. 9, 2006

Related U.S. Application Data

(60) Provisional application No. 60/724,579, filed on Oct. 7, 2005.

(51) Int. Cl.
*A61M 37/00* (2006.01)

(52) U.S. Cl. .................... 604/23; 315/111.21

(58) Field of Classification Search ............ 604/23, 604/24, 500, 501; 315/111.21, 111.81, 111.01, 315/111.51; 422/44; 606/45; 250/423 F
See application file for complete search history.

(56) References Cited

U.S. PATENT DOCUMENTS

| | | | |
|---|---|---|---|
| 3,437,864 A | 4/1969 | Kofoid et al. | |
| 4,088,926 A | 5/1978 | Fletcher et al. | |
| 5,147,493 A | 9/1992 | Nishimura et al. | |
| 5,198,724 A | 3/1993 | Koinuma et al. | |
| 5,285,046 A | 2/1994 | Hansz | |
| 5,309,063 A | 5/1994 | Singh | |
| 5,414,324 A | 5/1995 | Roth et al. | |
| 5,789,867 A | 8/1998 | Westendorp et al. | |
| 5,961,772 A | 10/1999 | Selwyn | |
| 5,977,715 A | 11/1999 | Li et al. | |
| 6,204,605 B1 | 3/2001 | Laroussi et al. | |
| 6,262,523 B1 | 7/2001 | Selwyn et al. | |
| 6,465,964 B1 | 10/2002 | Taguchi et al. | |
| 6,475,215 B1 * | 11/2002 | Tanrisever | 606/45 |
| 6,730,238 B2 | 5/2004 | Li et al. | |
| 2002/0129902 A1 | 9/2002 | Babayan et al. | |
| 2006/0156983 A1 | 7/2006 | Penelon et al. | |
| 2007/0029500 A1* | 2/2007 | Coulombe et al. | 250/423 F |

FOREIGN PATENT DOCUMENTS

AU 2006220583 A1 * 9/2006

OTHER PUBLICATIONS

Inomata et al., Open air deposition of SiO2 film from a cold plasma torch of tetramethoxysilane-H2-Ar system, Appl. Phys. Lett., Jan. 3, 1994, pp. 46-47, 64(1).

Koinuma et al., Development and application of a microbeam plasma. generator, Appl. Phys. Lett., Feb. 17, 1992, pp. 816-817, 60(7).

Appleby, USA Today, Jul. 13, 2005, p. 3B.

Gladwin et al., in "Clinical Microbiology Made Ridiculously Simple," MedMaster, Inc., Miami, FL, 2004.

(Continued)

*Primary Examiner* — Kevin C Sirmons
*Assistant Examiner* — Imani Hayman
(74) *Attorney, Agent, or Firm* — Canady & Lortz LLP; Bradley K. Lortz

(57) ABSTRACT

Apparatuses and methods for treating wounds are disclosed. An apparatus for treating wounds is disclosed comprising an instrument for generating a low temperature, atmospheric pressure plasma, a means of flowing gas through the instrument, and a means of contacting the wound with the reactive gases flowing out of the instrument. A method for treating wounds using reactive gases is disclosed. The use of atmospheric pressure plasmas for treating wounds is also disclosed.

22 Claims, 11 Drawing Sheets

OTHER PUBLICATIONS

Soejima et al., "Role of Nitric Oxide in Vascular Permeability after Combined Burns and Smoke Inhalation Injury," Amer. J. of Resp. and Cr. Care Med., vol. 163, p. 745, 2001.

Wolcott, "Biofilm Based Wound Care," Southwest Regional Wound Care Center, Lubbock, TX, 2005.

Costerton et al., "Bacterial Biofilms: A common cause of persistent infections," Science, vol. 284, p. 1318, 1999.

Laroussi, IEEE Transactions on Plasma Science, vol. 30, p. 1409, 2002.

Kelly-Wintenberg et al., Journal of Industrial Microbiology and Biotechnology, vol. 20, p. 69, 1998.

Herrmann et al., Physics of Plasmas vol. 6, p. 2284, 1999.

Abramzon et al., "Biofilm Destruction by RF High-Pressure Cold Plasma Jet," IEEE Trans. on Plasma Science, vol. 34, No. 4, Aug. 2006.

Shekhter et al., "Beneficial effect of gaseous nitric oxide on the healing of skin wounds," Nitric Oxide, vol. 12, p. 210, 2005.

* cited by examiner

US 8,267,884 B1

WOUND TREATMENT APPARATUS AND METHOD

CROSS-REFERENCE TO RELATED APPLICATION

This application claims the benefit under 35 U.S.C. §119 (e) of the following U.S. provisional patent application, which is incorporated by reference herein:

U.S. Provisional Patent Application No. 60/724,579, filed Oct. 7, 2005, and entitled "WOUND TREATMENT DEVICE AND METHOD", by Robert F. Hicks.

BACKGROUND OF THE INVENTION

1. Field of the Invention

The invention is related to methods and apparatuses for treating infections in living tissue, such as may occur in wounds. Particularly, the invention is related to methods and apparatuses for promoting wound healing by utilizing low temperature, atmospheric pressure plasmas. The invention also is related to a new use of atmospheric pressure plasmas for living tissue treatment.

2. Description of the Related Art

Wounds are a major source of infection. Once infected, wounds heal slowly, and if not treated aggressively can lead to amputation and even death. Recently, it was reported that in Pennsylvania alone, over 11,600 hospital patients became infected, leading to an additional 1,500 deaths and $2 billion in hospital charges (see e.g., USA Today, Jul. 13, 2005, page 3B). There are many different types of wounds, including surgical wounds, burns, ulcers, compound fractures, bedsores, and tissue necroses. Chronic skin ulcers are common in patients with reduced blood circulation due to diabetes mellitus, atherosclerosis, arteriosclerosis obliterans, Buerger's disease, and excessive radiation therapy. Skin ulcers are highly susceptible to infection. Infected wounds can cause secondary infections in other parts of the body, such as in the bone or bone marrow in osteomyelitis.

Soldiers receive complicated invasive wounds from gunshots, incendiary devices, improvised explosive devices (IEDs), land mines, and many other types of ordinance. Infection can set in at any time as the soldier is moved from the battlefield to the field hospital to recovery facilities. Once infected, battlefield wounds heal slowly, and treatment is a painful, prolonged process.

A variety of bacteria can invade wounds and prevent them from healing. These bacteria may be classified as gram-positive or gram-negative, and as obligate aerobes, facultative anaerobes, microaerophilic, or obligate anaerobes (see Gladwin and Trattler, in "Clinical Microbiology Made Ridiculously Simple," MedMaster, Inc., Miami, Fla., 2004). Among these, the microorganisms most likely to infect tissue, including skin and bone, are *Streptococcus pyogenes, Staphylococcus aureus, Clostridium perfringens,* and *Pseudomonas aeruginosa*. Skin infections from *Streptococcus* and *Staphylococcus* can result in impetigo, cellulitis, abscesses, furuncles, and carbuncles. *Streptococcus* can enter deep wounds and spread rapidly through the fascia between the skin tissue and muscle, causing Necrotizing Fasciitis, a condition that results in skin death and is often fatal. *Clostridium perfringens,* otherwise known as Gas Gangrene, invades deep wounds with dead tissue, where an anaerobic environment exists. This infection used to be common among soldiers wounded in battle.

*Pseudomonas aeruginosa* is common in hospitals, infecting sick patients with weak immune systems. This bacterium is a gram-negative, obligate aerobe. It is resistant to nearly all antibiotics. Diabetic patients have an increased risk of developing foot ulcers colonized with *Pseudomonas*, and it can penetrate into the bone causing osteomyelitis. This bacterium is very common in burned tissue, infecting over $\frac{1}{5}^{th}$ of all burn victims (see Kluytmans, "Surgical infections including burns," in *Prevention and Control of Nosocomial Infections*, Wenzel, ed., Williams and Wilkins, Baltimore, Md., 1997). If not eradicated, this infection eventually leads to fatal sepsis. Another microorganism that can similarly infect burns is *Pseudomonas cepacia*.

When bacteria invade wounds, they can quickly develop into a biofilm (see Wolcott, "Biofilm Based Wound Care," Southwest Regional Wound Care Center, Lubbock, Tex., 2005). A biofilm is a multicellular organism with strong defenses that makes eradication difficult, and is one of the main reasons chronic wounds do not heal (see Costerton, Stewart, and Greenberg, "Bacterial Biofilms: A common cause of persistent infections," Science, Vol. 284, p. 1318, 1999). *Pseudomonas aeruginosa* is an excellent example of biofilm forming bacterium, and is why this infection is so tenacious in ulcers and burned tissue. In order to treat, biofilm-based infections in wounds, a multi-pronged approach is needed that includes mechanical debridement (cutting and scraping), antibiotics, and topical antimicrobial agents. The former technique can be painful for the patient, and the wound can become infected again shortly after treatment. Moreover, bacteria are constantly evolving and in some cases are showing increased resistance to antibiotics and antimicrobial agents. Therefore, it is clear that new treatments are necessary to kill bacteria that invade wounds, and to further assist the body in the healing process.

Over the past several years, it has been shown that bacteria can be destroyed by exposure to atmospheric pressure plasmas (see for example, Laroussi, IEEE Transactions on Plasma Science, Vol. 30, p. 1409, 2002; Kelly-Wintenberg, Montie, et al., Journal of Industrial Microbiology and Biotechnology, Vol. 20, p. 69, 1998; and Herrmann, Henins, et al., Physics of Plasmas Vol. 6, p. 2284, 1999). The gas in these plasmas is weakly ionized so that the temperature remains low, i.e., near ambient conditions. In these studies, atmospheric pressure plasmas have been used to kill microorganisms dispersed on gel or glass media. Researchers have found that the effectiveness of the technique varies widely depending on the culture medium and how it is prepared, the specific plasma device used, and the method of plasma generation. Note that none of these studies focused on bacteria commonly found in wounds. In one case, the treatment of biofilms with atmospheric pressure plasma was examined (see Joaquin, Abramzon, and Brelles-Mariño "Gas Discharge Plasmas as a Novel Approach to Destroy Bacterial Biofilms," Applications in Environmental Microbiology, submitted in 2005). The researchers found that exposure of *Rhizobium gallicum* biofilm to the plasma for 5.0 minutes killed from 96.9 to 99.9% of the colony forming units.

A group of Russian researchers have shown that treatment of purulent wounds in rats with gaseous nitric oxide reduced healing time by 32% compared to the control group (see Shekhter, Serezhenkov, et al., "Beneficial effect of gaseous nitric oxide on the healing of skin wounds," Nitric Oxide, Vol. 12, p. 210, 2005). The nitric oxide was dispensed onto the wound at levels near 1000 ppm, and was produced using an air plasma device. These authors stated that they have treated over 10,000 patients with a wide variety of skin wounds, finding that gaseous nitric oxide promotes wound healing in most cases. Nevertheless, NO treatment of wounds has not proven to be effective in studies conducted in the United States, and in some cases, such as in burn injury, it could be detrimental to the patient (see Soejima, Traber, et al., "*Role of Nitric Oxide in Vascular Permeability after Combined Burns and Smoke Inhalation Injury*," American Journal of Respiratory and Critical Care Medicine, Vol. 163, p. 745, 2001).

Due to the widespread infection of wounds, and their annual toll on human life, not to mention the enormous costs to the medical profession and society in general, there is a great need in the art to develop more effective methods of treating these injuries. These and other needs are met by the present invention as described in detail hereafter.

SUMMARY OF THE INVENTION

To overcome the limitations in the prior art discussed above, and to overcome other limitations that will become apparent upon reading and understanding the specification, various embodiments of the present invention are directed to an apparatus for treating wounds, a method of treating wounds with gaseous radicals and other reactive species, and a new use of atmospheric pressure plasmas for wound treatment. The wound treatment apparatus comprises an instrument for generating a low temperature, atmospheric pressure plasma with a gas beam containing a high concentration of reactive species, such as oxygen radicals, and a means of contacting the wound with the gas beam, wherein the wound is bathed in the reactive species contained with in the gas beam. The radicals and other reactive species will kill bacteria present in the wound, destroy bacterial biofilms, and promote the healing of damaged tissue.

The method of treating wounds comprises flowing gas containing molecules, such as oxygen, through a device that is capable of dissociating the molecules into radicals and other reactive species, then directing the gas flow, which is rich in the radicals and other reactive species, out of the device and towards a wound, and exposing the wound to the reactive gas for a sufficient period of time to cause a therapeutic effect. The new use of atmospheric pressure plasmas comprises applying the reactive species generated in these devices to the direct treatment of wounds in skin, bone and other organs for the purposes of sterilization and promotion of the healing process.

One exemplary embodiment of the present invention is a wound treatment device that bathes the wound in reactive species, such as oxygen or hydroxyl radicals, at temperatures that are compatible for exposure to skin and other organs. This device comprises an instrument that generates a low temperature, atmospheric pressure plasma, wherein the radicals and other reactive species formed in the plasma flow out of the instrument in such a way that they come in direct contact with the wound. A particularly well-suited instrument for this embodiment is one that may be held in the hand or easily manipulated by the hand over the surface of the wound.

A further embodiment of the invention is an apparatus that comprises a low temperature, atmospheric pressure plasma with a gas beam containing radicals and other reactive species, and a fixture that mounts the plasma instrument directly above the wound surface, wherein the physician or medical technician is provided with a convenient and effective means of bathing the wound in the reactive species generated by the plasma. In a preferred embodiment the fixture may be detached from the instrument and disposed of so that there is no possibility of transferring bacteria from one patient to another. In another preferred embodiment the fixture may be detached from the instrument and sterilized for reuse on patients.

Another exemplary embodiment of the present invention is a method of treating wounds comprising flowing gas containing molecules, such as oxygen, through an atmospheric pressure plasma device that is capable of dissociating the molecules into radicals and other reactive species, for example O atoms, then directing the gas flow out of the device and towards a wound, and exposing the wound to the gas containing the reactive species for a sufficient period of time to kill bacteria and bacterial biofilms, and promote the healing of the wound. A particularly advantageous embodiment is where the plasma is generated in the vicinity of the outlet of the device so that a high concentration of radicals and other reactive species contacts the wound and effectively kills the bacteria and accelerates the healing process.

In a further embodiment of the invention, the instrument for generating gaseous reactive species is combined with a spray device so that the wound may be intermittently bathed with the gaseous reactive species and with a saline solution or a therapeutic chemical compound that helps promote wound healing. In this embodiment, the wound treatment apparatus comprises an instrument for generating a low temperature, atmospheric pressure plasma with a gas beam containing a high concentration of reactive species, a spray system for introducing a saline solution or a therapeutic chemical compound, a means of contacting the wound with the gas beam, and a means of contacting the wound with the spray solution, wherein the wound is alternately bathed in the gaseous reactive species and the saline solution or the therapeutic chemical compound.

In another embodiment, the invention comprises a method of wound treatment comprising flowing gas containing molecules through a device that converts the molecules into radicals and other reactive species, flowing the gas rich in the radicals and reactive species over the wound for a sufficient period of time, then briefly contacting the wound with a saline solution or a therapeutic compound, such as an antimicrobial agent, and repeating this procedure for one or more times, wherein the wound is sterilized and treated to promote the healing process. These and other embodiments of the present invention will be further understood upon inspection of the drawings and the accompanying description.

A typical embodiment of the invention comprises a plasma generating device for producing a flow of gas comprising at least one reactive gas species and a nozzle coupled to the plasma generating device for delivering the at least one reactive gas species to a wound. A gas flow system may be used to provide the flow of the gas to the plasma generating device. The gas flow system may incorporate a compressor and/or tanks of compressed inert gases (e.g. argon) and oxygen gas and one or more metering valves to control the gas composition and flow rate. For example, the at least one reactive gas species may be selected from the group consisting of oxygen atoms, nitrogen atoms, hydrogen atoms, and hydroxyl radicals. In addition, the apparatus can employ an electrical power supply coupled to the plasma generating device for generating the at least one reactive gas species (e.g. through application of a high frequency voltage applied across the gas flow).

The nozzle for delivering the at least one reactive gas species to the wound may comprise a shape selected from the group consisting of a disc, a rectangle, a cone and a hemisphere. The shape has at least one opening for the reactive gas species to flow out. The disc and hemispherical shapes may have a plurality of holes. The rectangular shape may have a slit. The cylindrical shape may have a single hole. In addition, a detachable end cap over the nozzle may be used for protecting the wound from cross-contamination among different patients.

Further embodiments of the invention may also employ the plasma generating device as a hand-held device held and manipulated by a user to deliver the at least one reactive gas species to the wound of a patient. Other embodiments may incorporate a robotic arm coupled to the plasma generating device for scanning the at least one reactive gas species over the wound.

Some embodiments may also utilize a control unit coupled to the plasma generating device for supplying the gas flow and gas composition and electric power to the plasma generating device for generating the at least one reactive gas species.

In still further embodiments, an internal cooling system may be used comprising a cooling fluid circulating around the nozzle to cool the flow of the gas. The cooling system reduces the temperature of the delivered reactive gas species contacting the wound.

In yet further embodiments, an exhaust gas system may be used for drawing any potentially harmful gases in the gas flow including the at least one reactive gas species away from a patient with the wound.

In addition, embodiments of the invention may employ a proximity sensor for providing a feedback signal indicating proximity of the nozzle to the wound. The proximity sensor allows an operator to confirm that an adequate supply of the at least one reactive gas species is delivered to the wound as the reactive gas dissipates quickly outside a relatively short effective range.

In still further embodiments of the invention, the nozzle may incorporate a chemical outlet for delivering a chemical compound to the wound. The at least one reactive gas species may be selected to cause the chemical compound to bond to cells of the wound.

In a similar manner, a typical method embodiment of the invention may comprise the operations of flowing a gas, generating a low temperature, atmospheric pressure plasma, forming at least one reactive gas species in the low temperature, atmospheric pressure plasma, and delivering the at least one reactive gas species to a wound. Method embodiments of the invention may be further modified consistent with apparatus embodiments of the invention described herein.

DETAILED DESCRIPTION

In the following description including the preferred embodiment, reference is made to the accompanying drawings, which form a part hereof, and in which is shown by way of illustration a specific embodiment in which the invention may be practiced. It is to be understood that other embodiments may be utilized and structural changes may be made without departing from the scope of the present invention.

1.0 Overview

Figure 1:
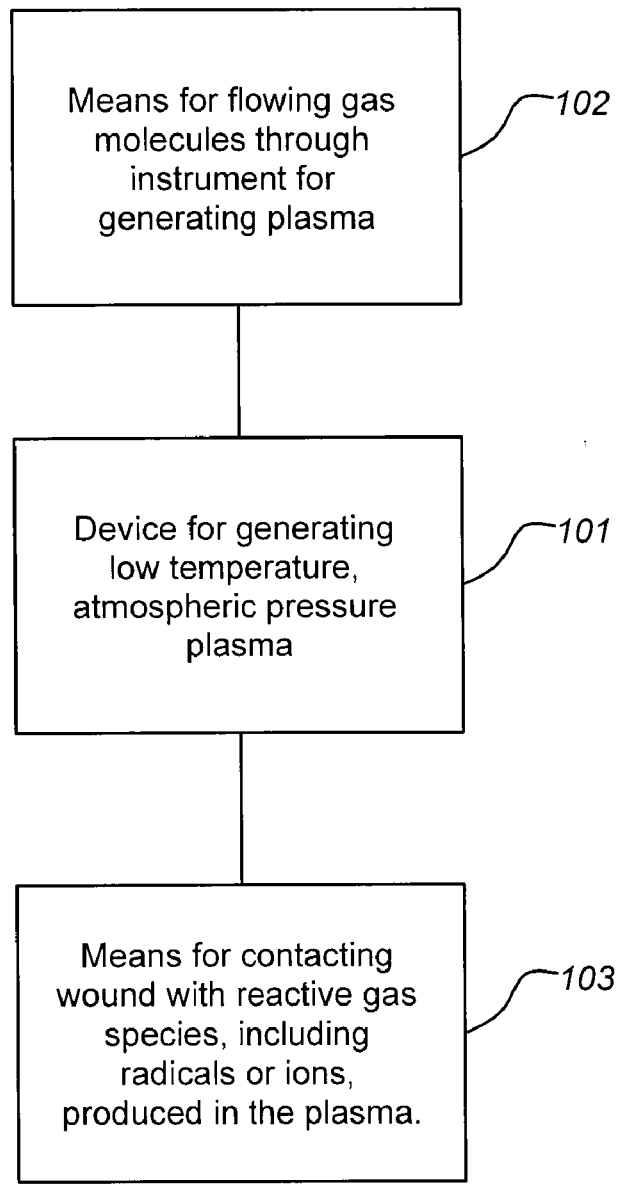
FIG. 1 is a block diagram of the wound treatment apparatus in accordance with the present invention.

FIG. 1 shows a block diagram of an exemplary embodiment of the present invention. The apparatus comprises an instrument 101 for generating a low temperature, atmospheric pressure plasma coupled to a means 102 for flowing gas containing molecules through the instrument 101, and a means 103 of contacting the wound with the reactive gas species generated in the plasma. For the purposes of the present invention reactive gas species include, but are not limited to, radicals, ions, ground-state atoms, or metastable molecules. The instrument for generating the low temperature, atmospheric pressure plasma generally comprises electrodes that are connected to an electrical power source. The power source can provide a DC voltage, an AC voltage, or a high-frequency voltage operating from 5 kHz to 500 MHz. The electrodes are arranged in such a way and the voltage is supplied at a sufficiently high value, such that the gas is partially ionized and converted into the low temperature, atmospheric pressure plasma, i.e. comprising at least one reactive gas species.

The means 102 for flowing gas containing molecules through the instrument 101 comprises a source of one or more gases that is pressurized above atmospheric pressure, or a means of pressurizing a source of one or more gases above atmospheric pressure, a device for controlling the flow of one or more gases, a means of mixing the gases if more than one in used, and tubing or piping that connects the mixed, flowing gases to the instrument 101. An exemplary embodiment of the means 102 comprises a source of air, a compressor to increase the pressure of air above atmospheric pressure, a metering valve that regulates the flow of air, and that delivers the air from the compressor through the metering valve and into the instrument 101. Another exemplary embodiment of the means 102 comprises a tank of compressed inert gas, such as argon, a second tank of compressed oxygen gas, pressure regulators attached to each tank to ensure delivery of the gases at a constant pressure above atmospheric pressure, a metering valve that regulates the flow of inert gas, a second metering valve that regulates the flow of oxygen gas, a "tee" fitting that combines the inert gas and oxygen flows together, and tubing that delivers the gases from the pressure regulators through the metering valves and into the instrument 101. Other fitting and devices may be added to otherwise improve the means of flowing gas to the instrument, such as a purifier, filter, flow sensor, check valve, and pneumatic on and off valves, and will be understood by those skilled in the art.

The means 103 of contacting the wound with the reactive gas species generated in the plasma entails configuring the instrument in such a way that the transit time of the reactive gas species from the exit of the plasma device to the wound is short enough to prevent the reactive gas species from being converted back into stable molecules prior to impinging on the wound. The transit time is generally less than 0.05 seconds, and preferably less than 0.01 seconds (10.0 milliseconds). The means 103 of contacting the wound with the reactive gas species generated in the plasma may be accomplished in many different ways. An exemplary means comprises generating the plasma just prior to the gas outlet from the instrument 101, placing the outlet of the instrument above the wound at a distance of 0.1 to 10.0 cm, and providing sufficient gas velocity at the outlet that the transit time from the instrument 101 to the wound is less than 0.05 seconds, and preferably less than about 10.0 milliseconds. The means of placing the instrument above the wound may comprise holding it with the hand, mounting it in a fixture that can be positioned over the wound, mounting it in a robotic mechanism that may be controlled with a computer, or inserting it in a fixture that can be attached to the patient around the area of the wound. Other means of placing the instrument above the wound may be used without deviating from the scope of the present invention, and would be obvious to those skilled in the art.

Some embodiments of the invention may be implemented using low-temperature atmospheric plasma devices and methods taught in U.S. patent application Ser. No. 11/227,724 by Penelon et al., filed Sep. 9, 2005 and entitled "LOW TEMPERATURE, ATMOSPHERIC PRESSURE PLASMA GENERATION AND APPLICATIONS," and U.S. patent application Ser. No. 11/532,749 by Babayan et al., filed Sep. 18, 2006 and entitled "LOW-TEMPERATURE, CONVERGING, REACTIVE GAS SOURCE AND METHOD OF USE," which are both incorporated by reference herein. Particularly, devices are taught which can be used to contact a wound with at least one reactive gas species with an adequately short transit time to enhance effectiveness of the treatment. U.S. patent application Ser. No. 11/532,749 teaches closely spaced electrodes may comprise a surface of a curved electrode (i.e. a first electrode) and a surface of a housing (i.e. a second electrode) machined into the same shape forming a uniform gap between the surfaces in contact with the gas flow where the low temperature, atmospheric pressure plasma is generated.

2.0 Wound Treatment Apparatus

Figure 2:
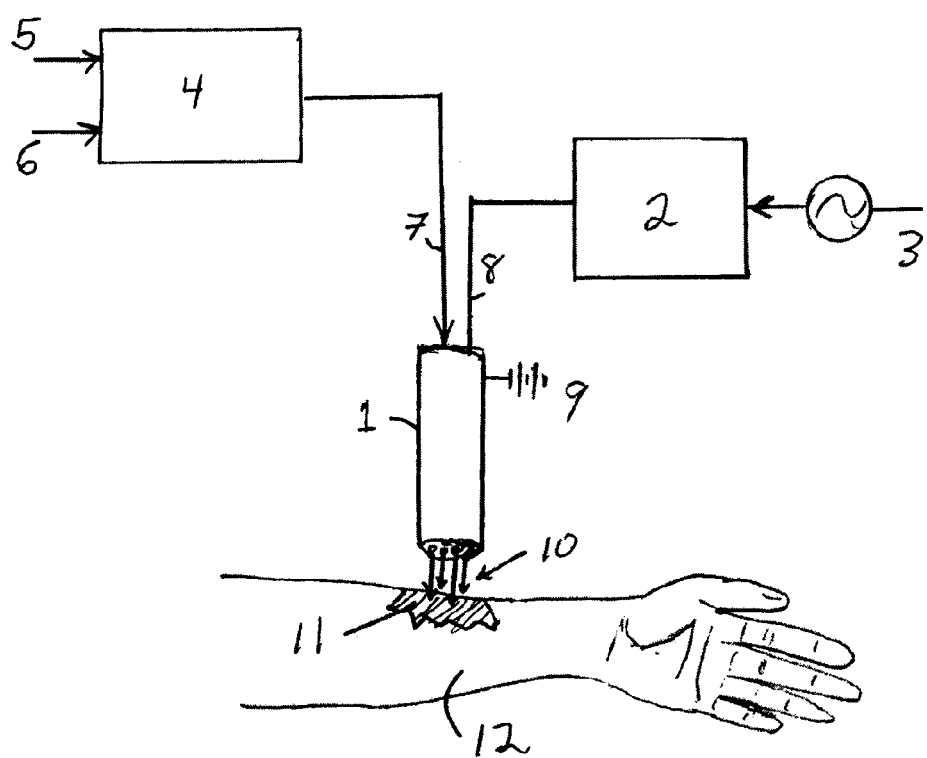
FIG. 2 is a schematic of the wound treatment apparatus in accordance with the present invention.

A schematic of the wound treatment apparatus in accordance with the present invention is shown in FIG. 2. In this figure, the self-contained, low temperature, atmospheric pressure plasma source 1 is connected via a flexible cable 8 to an electrical power supply 2 that receives electricity from a standard AC outlet 3. It is advantageous that the housing of the plasma source 1 be grounded 9, so that there is no danger of electrical shock to the user of the apparatus. The plasma source 1 is also connected via flexible tubing 7 to a gas flow system 4 that is supplied with inert gas through feed line 5 and with oxygen gas through feed line 6. Examples of inert gas include, but are not limited to, argon and helium. Other reactive gases that may be supplied to the plasma through feed line 6 include, but are not limited to, air, carbon dioxide, carbon monoxide, hydrogen, nitrogen, nitrous oxide, ammonia, and water. Note that the electrical power supply 2 and the gas flow system 4 may be combined in a single control box for convenience. The low temperature, atmospheric pressure plasma 1 is positioned within a few centimeters of the wound 11 on a patient's arm 12. Reactive gas 10 from the plasma source 1 bathes the wound 11, killing bacteria and treating the wound to promote healing.

Figure 3:
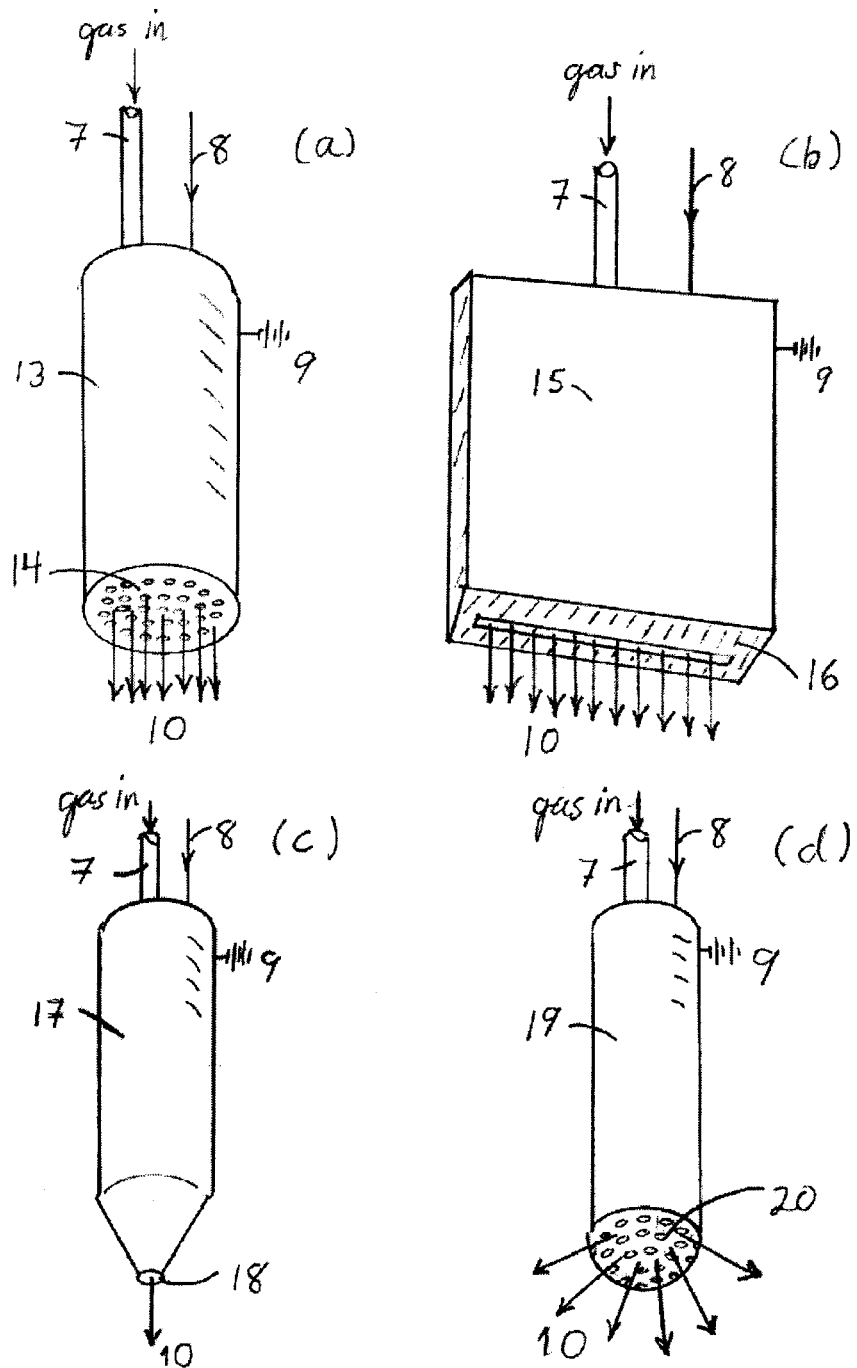
FIG. 3 shows schematics of different wound treatment apparatuses with (a) circular, (b) linear, (c) small-spot, and (d) hemispherical plasma beams.

Exemplary embodiments of the present invention are presented in FIG. 3. The self-contained, low temperature, atmospheric pressure plasma may be configured in a variety of different shapes and sizes, depending upon the type and size of wound to be treated. In schematic 3(a), the device housing 13 exhibits a cylindrical shape and contains a gas outlet nozzle 14 that is disk shaped and has a plurality of holes in it. Other types of perforations may be machined into the outlet nozzle 14, such as ellipses, triangles, polygons, slits and annular rings without deviating from the scope of the present invention. The purpose of the disk shaped nozzle 14 is that is produces a shower of reactive gas 10 that is evenly distributed over the area of the wound. The diameter of the cylindrical housing 13 and nozzle 14 may vary from about 0.5 cm to about 6.0 cm, depending on the area of the wound to be treated, as will be understood by those skilled in the art. The gas feed and electrical signal to the plasma source are introduced through the tubing 7 and the cable 8, respectively. Also, the housing is grounded 9. During operation of the device, the reactive gas 10 generated by the plasma is passed over the wound to sterilize and promote healing.

In schematic 3(b), the device housing 15 has a rectangular shape and contains a gas outlet nozzle 16 that has a slit in it. This design generates a linear curtain of reactive gas 10 that can be swept back and forth over the wound. Other perforations may be machined into the outlet nozzle 16 to produce the desired linear curtain of reactive gas, without deviating from the scope of the present invention. These perforations may be a series of holes in a row that are round, square, triangular, rectangular, polygonal, or irregularly shaped. In addition, there may be more than one row of perforations, generating more than one linear curtain of reactive gas 10. The width of the rectangular housing 13 and in turn the slit in the nozzle 16 may vary from about 0.5 cm to about 10.0 cm, depending on the area of the wound to be treated, and would be obvious to those skilled in the art. The gas is fed to the device through tubing 7, the electrical signal is introduced through cable 8, and the housing is grounded 9.

In schematic 3(c), the device housing 17 exhibits a cylindrical shape and comprises a gas outlet nozzle 18 that has a single, small hole. The diameter of the nozzle 18 may be made small, less than 5.0 mm, and preferably less than 2.0 mm, in order to treat a small spot on the patient with the reactive gas 10. In a preferred embodiment of the present invention, the diameter of the housing 17 may be made small and lengthened, if necessary, so that the device may be inserted inside a patient to treat an internal wound, such as might be found in cases of osteomyelitis. The outlet hole in the nozzle 18 may have shapes other than a circular disk, including, but not limited to ellipses, slits, triangles, rectangles, polygons, and annular rings. The gas feed and electrical signal are introduced through the tubing 7 and the cable 8, and the housing is grounded 9.

In schematic 3(d), the device housing 19 is cylindrically shaped and contains a gas outlet nozzle 20 that is hemispherical and has a plurality of holes in it. This design causes the reactive gas produced in the plasma to flow out in a radial direction over the surface of the hemisphere. Other types of perforations may be machined into the hemispherical outlet nozzle 20, such as ellipses, triangles, squares, polygons, and slits, without deviating from the scope of the present invention. The purpose of this design is to treat the interior surface of a deep wound, by inserting the nozzle 20 down inside the wound. Since the reactive gas 10 flows out in all directions, it will efficiently treat the exposed wound surfaces. The diameter of the housing 19 and the nozzle 20 may be made small, less than 5.0 mm, and preferably less than 2.0 mm, in order to insert the device inside a patient to treat an internal wound. Here as well, the gas is fed to the device through tubing 7, the electrical signal is introduced through cable 8, and the housing is grounded 9.

3.0 Treating an Injured Patient with the Wound Treatment Apparatus

Figure 4:
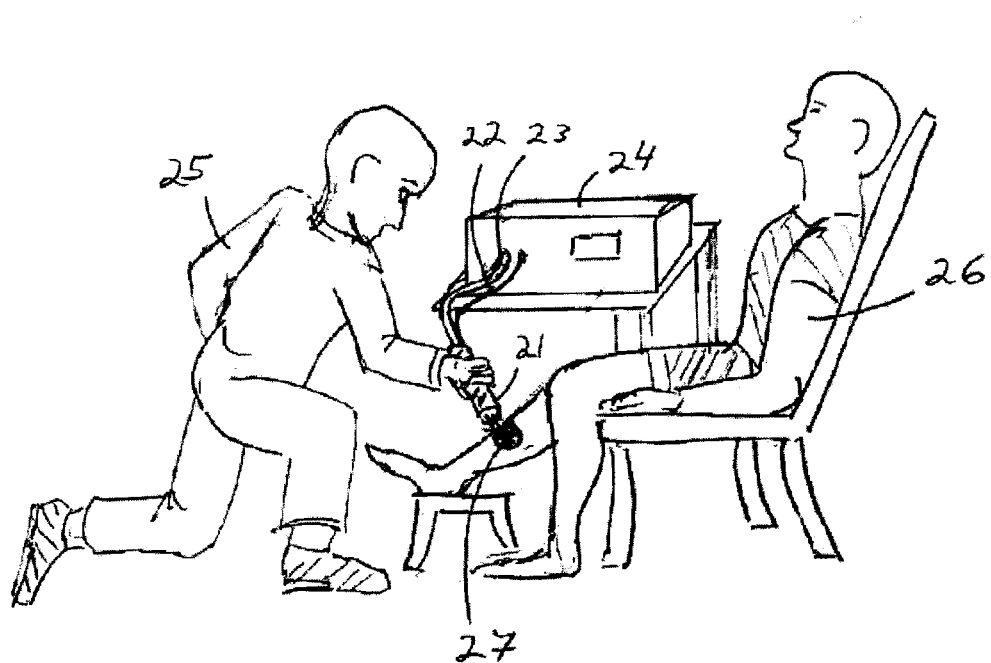
FIG. 4 is a drawing illustrating how a doctor or medical technician may use the wound treatment apparatus on an injured patient.

In one embodiment of the present invention, the wound treatment apparatus comprises a handheld tool for treating injured patients. A drawing showing a physician or medical technician employing the invention in this embodiment is shown in FIG. 4. The physician 25 is treating an ulcer 27 on the calf of a patient 26, such as might occur in a person with diabetes mellitus. The handheld device 21 is operated with a control unit 24 that provides a means of flowing gas through the device and a means of supplying an electrical voltage to the device sufficient to generate the plasma from the flowing gas. The tubing 23 connects the gas flow from the control unit 24 to the device 21. The cable 22 connects the electrical signal from the control unit 24 to the device 21. The physician 25 waves the wound treatment device 21 directly over the ulcer 27 bathing it in the reactive species generated from the plasma, thereby killing bacteria present in the wound, and aiding the healing process.

Figure 5:
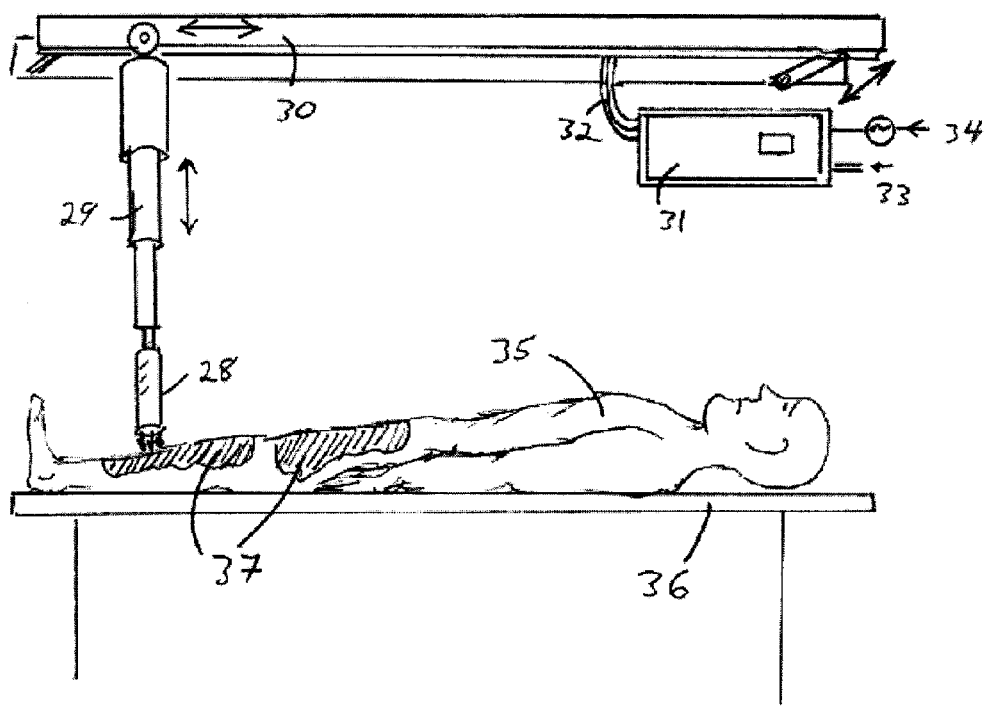
FIG. 5 is a drawing illustrating how a doctor or medical technician may use the wound treatment apparatus on a patient with a wound covering a large area, such as might occur with an extensive burn.

A schematic of an exemplary wound treatment apparatus configured for treating a patient with a wound covering a significant part of their body is presented in FIG. 5. The patient 35 has a severe burn 37 that extends over a large portion of the left leg. The patient 35 is lying on an examination table 36, so that the low temperature, atmospheric pressure plasma device 28 can scan over the burned area. The device 28 is attached to a telescoping robotic arm 29, which is in turn attached to a ceiling mounted, x-y translation system 30. The robot arm 29 and x-y translation system 30 may be computer controlled to scan in a precise manner over the affected area, and thereby provide the optimal therapeutic effect. The physician or medical technician assists this process by positioning the patient 35 on the table 36 and entering the instrument scanning parameters into the computer. In addition, the device 28 may be equipped with sensors that automatically adjust the apparatus's position above the wound through a feedback control system.

A control unit 31 is connected to the device 28 through flexible lines 32. The control unit 31 supplies the device 28 with the gas flow rate, gas composition and electrical power needed to operate the plasma. Gas is supplied to the system through the gas inlet 33, whereas electricity is provided by the AC power cord 34.

4.0 Wound Treatment Apparatus with Internal Cooling System

Figure 6:
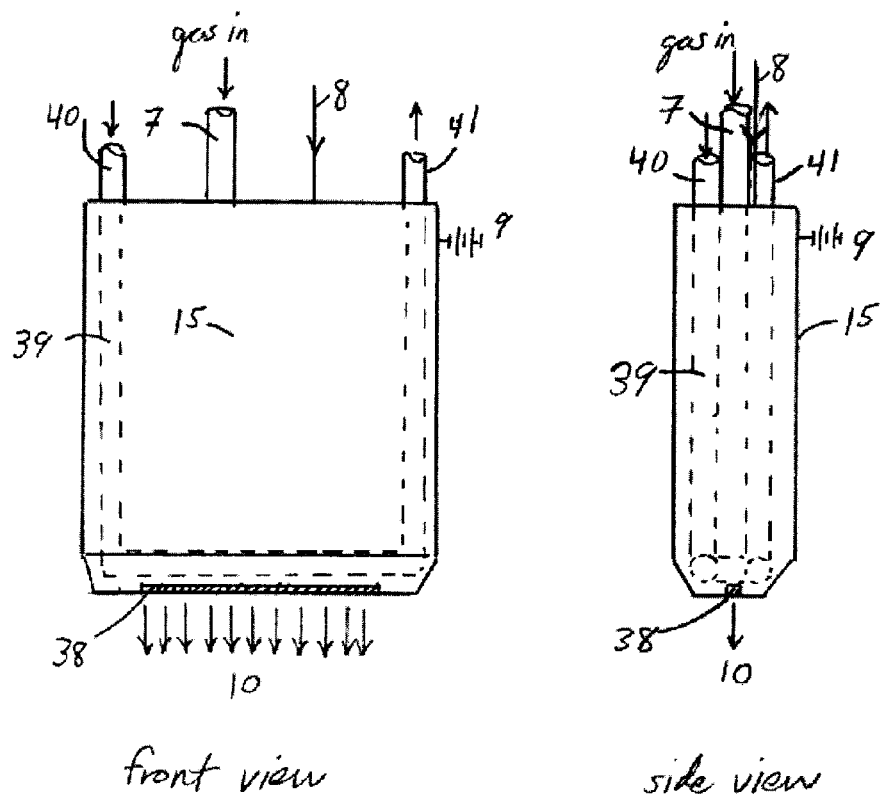
FIG. 6 is a schematic of a wound treatment apparatus equipped with a means of cooling the plasma generator.

In one embodiment of the present invention, the wound treatment apparatus is provided with an internal cooling system as shown in FIG. 6. The purpose of the internal cooling system is to provide a means of cooling the flow of gas exiting the plasma so that it can be maintained at a temperature close to that of the patient. Although the example shown in FIG. 6 is for a rectangular device with a linear reactive gas beam 10, the internal cooling system could be equally well adapted to atmospheric plasma sources (and/or nozzles) of any size or shape, including but not limited to, cylindrical housings with disk-shaped, small spot, or hemispherical nozzles as shown in FIG. 3. The rectangular housing 15 is configured with a gas inlet 7, electrical input 8, ground 9, and reactive gas outlet 38. The cooling system comprises an internal flow channel 39, inlet 40 and outlet 41.

The cooling fluid may be any gas or liquid that is supplied at or below room temperature. For example, air from a compressor may be supplied to the inlet 40. Alternatively, chilled water may be used to cool the device by connecting the inlet 40 and outlet 41 to a recirculating bath. The internal flow channel is placed near the outlet of the housing 15, so that it can cool the gas as it passes through the plasma and out the outlet slit 38. This ensures that the reactive gas beam is cooled most effectively. Other designs may accomplish the same means without departing from the scope of the present invention, as will be understood by those skilled in the art.

5.0 Wound Treatment Apparatus with Detachable Fixture

Figure 7:
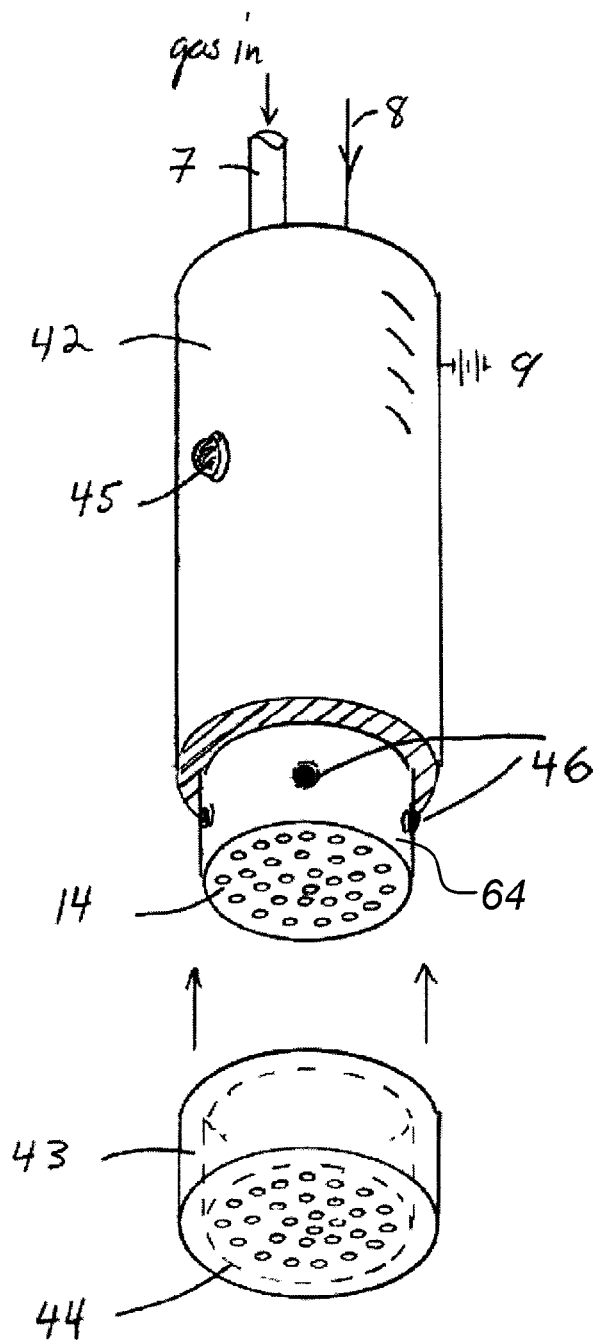
FIG. 7 is a schematic of a wound treatment apparatus equipped with a detachable fixture to prevent cross contamination between patients.

Another exemplary embodiment of the wound treatment apparatus is shown in FIG. 7. Here, the device for generating the plasma has a detachable end cap 43 that protects the patient from cross contamination. The cylindrical housing 42 has a larger diameter than the nozzle 14 so that there is a notched region 64 that inserts inside the end cap 43. The nozzle 44 of the end cap 43 is designed so that the holes match up with those on the nozzle 14 on the body of the plasma source. This ensures that the reactive gas beam is unimpeded upon flowing out of the device. The end cap 43 is held in place with spring-loaded buttons 46 distributed around the outside of the notched region 64. A button 45 on the housing 42 is depressed to retract the buttons 46 and allow the end cap 43 to be released from the device. The device is equipped with the gas inlet 7, electrical input 8, and ground 9 to enable operation of the low temperature, atmospheric pressure plasma.

The end cap 43 can be made of a metal, ceramic, or plastic material, and can be disposable so that it is only used on one patient. In this way, there is no way that microorganisms can be transferred from one patient to the next when using the wound treatment apparatus. In another embodiment, the end cap 43 can be made for use several times on the same patient with a simple cleaning of the end cap between uses. In yet another embodiment, the end cap 43 can be made for repeated use with sterilization of the end cap in an autoclave between uses. Sterilization will prevent bacteria from one patient's wound from cross-contaminating another patient's wound. It is envisioned that the doctor or medical technician will want to keep a number of end caps on hand, and always use a freshly sterilized one on each patient. It may be that the disposal end cap is the best approach to guarantee that there is no cross-contamination among patients.

The removable end cap 43 may be designed in a number of different ways without deviating from the scope of the present invention. The end cap 43 may be constructed to fit onto a cylindrical, elliptical, rectangular, square, or any arbitrarily shaped wound treatment apparatus. Preferably, the size and shape of the end cap 43 should be engineered to fit snuggly onto the wound treatment apparatus and have a nozzle design 44 that mates with the device nozzle 14 in such a way that the flow of reactive gas out of the device is not blocked by the end cap 43. Many different means of attaching and releasing the end cap from the wound treatment apparatus may be employed, including a set screw, metal or plastic clip, spring clamp, threaded connection, snap, and other connecting elements as will be understood by those skilled in the art.

6.0 Wound Treatment Apparatus with Exhaust Gas System

Figure 8:
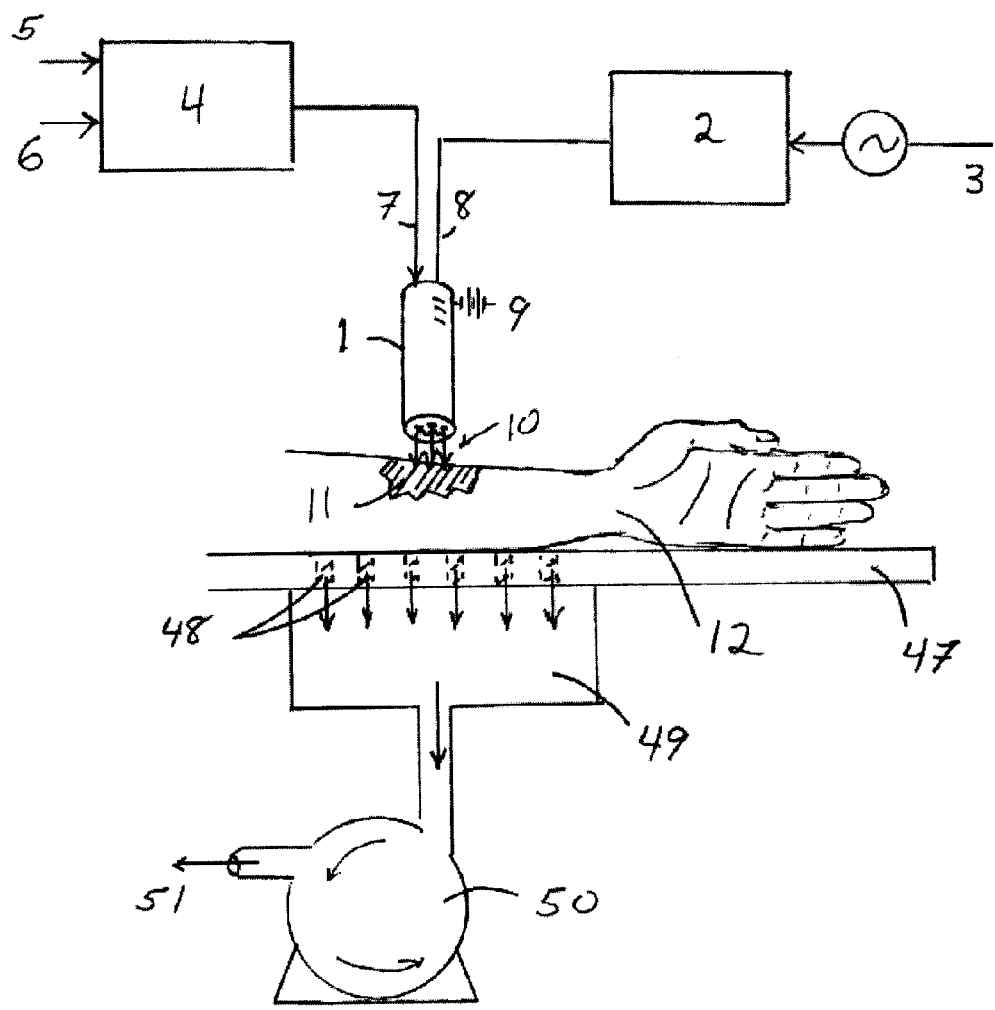
FIG. 8 is a schematic of a wound treatment apparatus equipped with an exhaust gas containment system.

Shown in FIG. 8 is a schematic of a wound treatment apparatus that incorporates a means of exhausting the gas from the plasma away from the patient and the room where the treatment is being performed. The purpose of the exhaust gas system is to ensure that the patient and the environment are not exposed to any potentially harmful gas molecules that are produced from the reactive species formed in the plasma. For example, air plasmas may produce ozone and nitric oxide, both of which can be harmful to humans if inhaled in sufficient quantity. Incorporation of an exhaust gas system into the wound treatment apparatus prevents exposure of the patient to any potentially harmful gases. The need for an exhaust gas system will depend upon the particular gas and/or byproducts in the particular application as will be understood by those skilled in the art.

In FIG. 8, the device 1 housing the low temperature, atmospheric pressure plasma is suspended above the wound 11 in the patient's arm 12. The device 1 is connected to an electrical power supply 2 via cable 8, and to a gas flow system 4 via flexible tubing 7. The electrical power supply is connected to a source of electricity with the power line 3. The gas flow system 4 has two gas supply lines 5 and 6, which for example, may be used to introduce helium and oxygen. The reactive gas 10 emanating from the plasma bathes the wound 11, killing bacteria and treating the wound to accelerate the healing process. Reactive gas flowing over the wound is pulled down through the holes 48 in the treatment table 47. A housing 49 encases the holes 48 so that the gas is substantially pumped away through a blower 50 and into a line 51 that exhausts the gas outside the room.

Other means of incorporating an exhaust gas system into the wound treatment apparatus may be devised without deviating from the scope of the present invention. For example, instead of connecting the blower 50 to the table 47 with holes 48, one may place a flexible duct on the end of the blower. Then the physician or technician can hold or mount the duct below the wound 11, while the plasma device 1 is suspended above it. In this way, the reactive gases 10 will flow out over the wound 11 and then be pulled down into the duct, and exhausted from the room.

7.0 Wound Treatment Apparatus with Sensor

Figure 9:
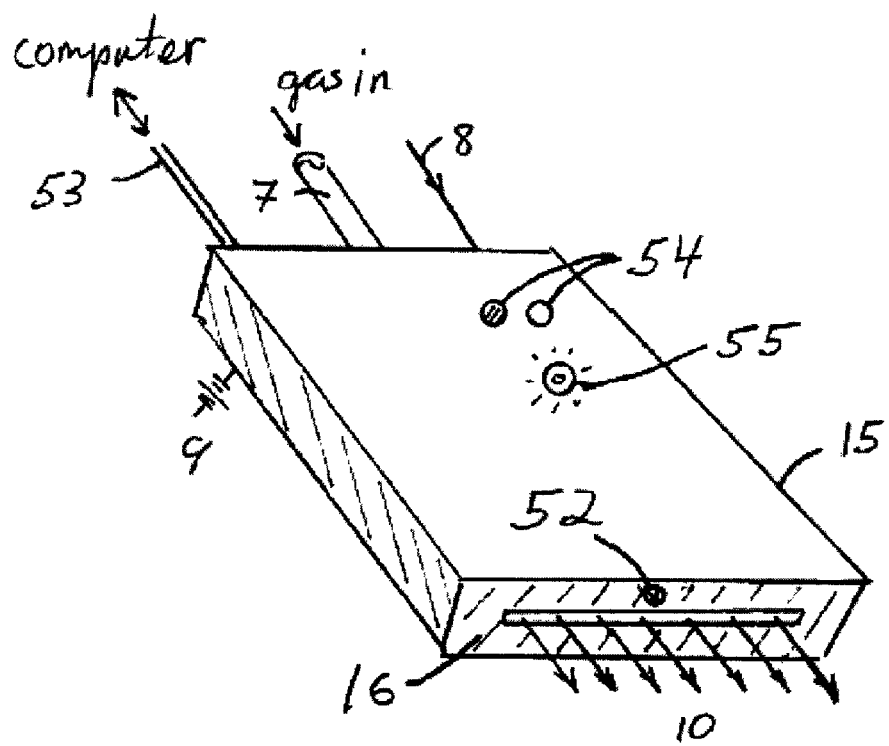
FIG. 9 is a schematic of a wound treatment apparatus equipped with a sensor for detecting the distance between the gas outlet of the apparatus and the wound surface.

In another embodiment of the present invention, the wound treatment apparatus may be equipped with a sensor to detect the distance of the apparatus from the wound surface. Since the reactive species generated by the plasma (including but not limited to radicals, ions, ground-state atoms or metastable molecules) decay rapidly upon exiting the plasma, it is important to hold the wound treatment apparatus within a few centimeters of the wound. This makes sure that a sufficient number of reactive species impinge on the wound to provide the therapeutic effect. Shown in FIG. 9 is a schematic of a wound treatment apparatus that incorporates a sensor. The proximity sensor 52 is mounted on the nozzle plate 16 of the rectangular plasma source housing 15. The sensor 52 views the wound in the same direction that the reactive gas 10 is flowing. The sensor 52 is connected to a computer through a cable 53. The computer receives the electrical signal from the sensor 52, interprets this data, and determines if the apparatus is being held within the desired distance from the wound. One may mount onto the housing 15 light-emitting diodes 54 and an audible horn 55 that notifies the operator when the apparatus is being held too far away from the wound to be effective. Many different types of sensors may be used to detect, record and notify the operator of the distance between the apparatus and the wound without deviating from the scope of the present invention, and will be understood by those skilled in the art.

Figure 10:
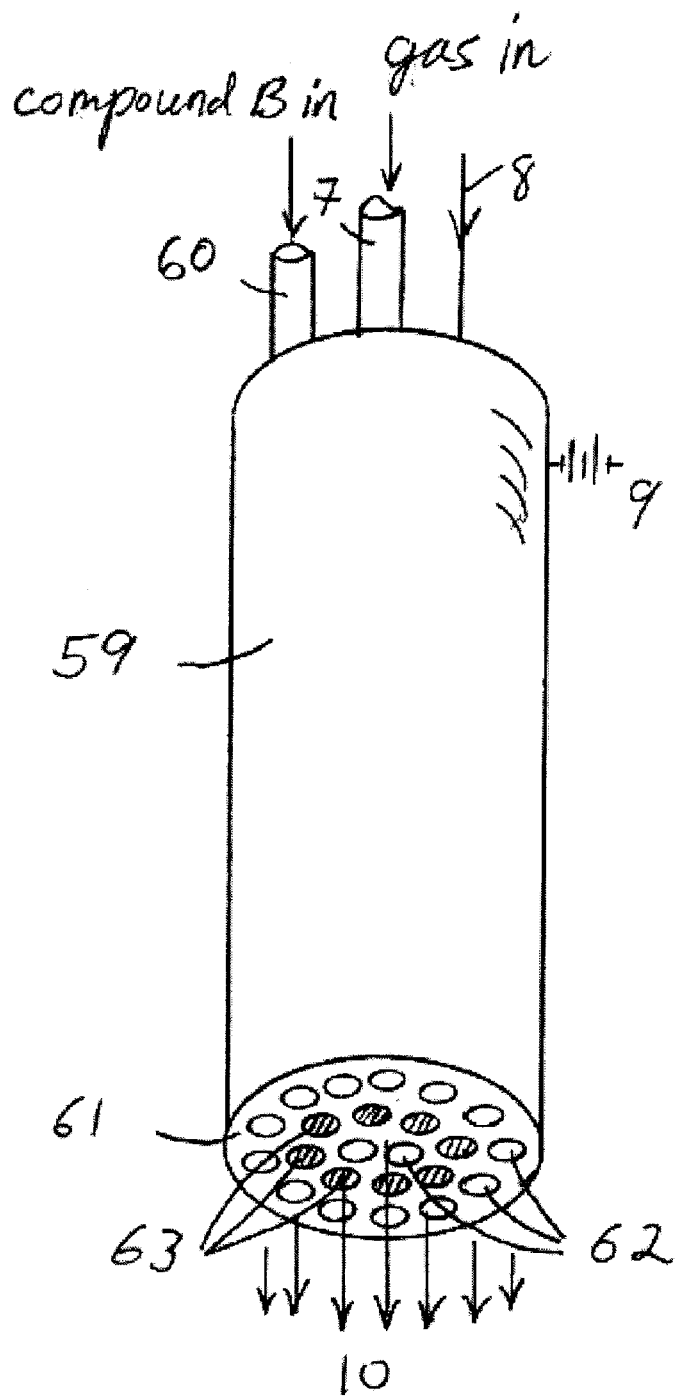
FIG. 10 shows a drawing of a wound treatment apparatus equipped with a means of both bathing the wound in the plasma and dispensing a chemical compound onto the wound.

8.0 Wound Treatment Apparatus with Plasma and Means of Dispensing Chemical Compound Another exemplary embodiment of the present invention is presented in FIG. 10. Here, the wound treatment apparatus combines a low temperature, atmospheric pressure plasma with a means of dispensing a chemical compound (B) onto the wound. The cylindrical device housing 59 contains internal electrodes for generating the plasma, a gas inlet 7, electrical input 8 that attaches the power supply to the electrodes, ground 9, inlet 60 for chemical compound B, and outlet nozzle 61. The outlet nozzle 61 is configured with two sets of holes: one set 62 for the plasma effluent, and a second set 63 for the chemical compound B. Inside the housing 59 and the nozzle 61 there are means of separately delivering the gas to the plasma and the outlet holes 62, and the chemical compound to the outlet holes 63.

The advantages of the embodiment disclosed in FIG. 10 is that the wound may be bathed alternately in the plasma reactive species 10, and in a therapeutic chemical compound B, thereby providing a more effective treatment. For example, the oxygen plasma generates O atoms and metastable $O_2$ molecules plus a small amount of heat. The flow of dry, warm gas over the wound tends to dry it out. To prevent the wound from drying out too much, chemical compound B may be a saline solution that is intermittently dispensed onto the wound from the apparatus. In another embodiment of the present invention, chemical compound B may be an antimicrobial agent or a drug that when deposited on the wound increases the destruction rate of bacteria, and accelerates the rate of wound healing.

In yet another embodiment of the present invention, chemical compound B may be a specific molecule that is designed to react with microorganisms and skin tissue that have been activated by exposure to the plasma. It is known that oxygen atoms and other radicals generated in atmospheric pressure plasmas react with polymer surfaces, creating oxygenated groups that alter the surface energy. Microorganisms and skin tissue are composed of large organic molecules that have a composition and structure that is similar to that of polymers. Therefore, brief exposure of microorganisms and skin tissue to the oxygen plasma will cause their surfaces to be covered with oxygenated groups. These groups can further react with drug molecules, causing them to strongly bond to the cell membranes. In the case of harmful bacteria, the drug molecules can be designed to be lethal to the organism once they are attached to the cell membrane. In the case of skin tissue, the drug molecules can be designed to deliver proteins and enzymes that will rejuvenate the cells, causing the wound to heal faster.

The schematic in FIG. 10 depicts one embodiment of the present invention for wound treatment by atmospheric pressure plasma combined with other topical chemical or drug therapies. This embodiment integrates the plasma and compound B delivery into one apparatus. Many other embodiments may be used without deviating from the scope of the present invention. For example, delivery of the plasma and the chemical compound B to the wound may be accomplished with separate apparatuses. The chemical compound B, e.g., saline solution, may be delivered to the wound through the use of a sterile gauze pad, an aerosol spray device, a needle and syringe, or any other practical instrument that would be obvious to those skilled in the art.

9.0 Wound Treatment Apparatus with Multiple Embodiments

Figure 11:
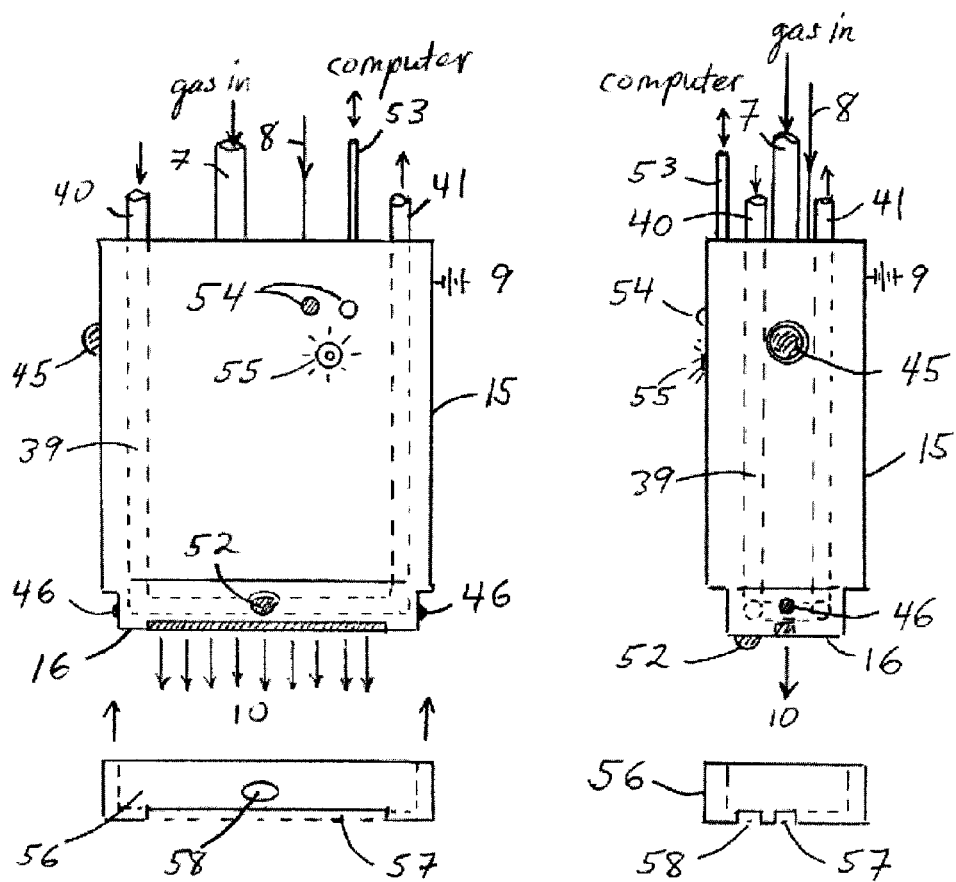
FIG. 11 is a schematic of a wound treatment apparatus that incorporates multiple elements according to the present invention.

The wound treatment apparatus may incorporate multiple embodiments of the present invention as depicted in FIG. 11. This wound treatment apparatus comprises a low temperature, atmospheric pressure plasma in a rectangular housing 15 that generates a linear reactive gas beam 10. The apparatus has the following additional embodiments: a detachable end cap 56 to eliminate the potential for spreading infection among different patients; an internal cooling system 39, 40 and 41 that keeps the temperature of the plasma gas close to that of the patient; and a sensor 52 that is connected to a computer and assists with maintaining the proper distance of the apparatus from the wound. Further embodiments of the invention, or alternative combinations and permutations of the various features of embodiments of the invention described herein may be employed without deviating from the scope of the present invention.

Note that the end cap 56 is designed to fit snuggly onto the outlet nozzle 16, and it contains a slit 57 that is at least as large as the gas flow slit in the outlet nozzle 16. The end cap 56 also has a hole that permits the sensor 52 to have an unobstructed view of the wound. Spring-loaded buttons 46 are distributed around the outside of the outlet nozzle 16. The button 45 on the housing 15 is depressed to retract the buttons 46 and allow the end cap 56 to be released from the device. The sensor 52 is connected to a computer through the cable 53. The computer receives the electrical signal from the sensor 52, interprets this data, and determines if the device is being held within the desired distance from the wound. In addition, the housing 15 contains light-emitting diodes 54 and an audible horn 55 that notifies the operator when the apparatus is being held too far away from the wound. Finally, the cooling medium, such as chilled water, is circulated into the housing 15 through the inlet port 40, down the flow channel 39, and out through the outlet port 41. As part of the atmospheric plasma generation system, the device contains a gas inlet 7, electrical input 8, and ground 9.

An exemplary embodiment of the present invention is for the wound treatment apparatus to contain the following elements: an outlet nozzle that effectively contacts the wound with the reactive gas species generated in the plasma; an internal cooling system; an end cap to prevent cross-contamination; a sensor to assist the operator with holding the device the proper distance from the wound, and an exhaust gas containment system to prevent exposure of patients or personnel to gas molecules, such as ozone, produced by the plasma. Another preferred embodiment of the present invention is for the wound treatment apparatus to contain these elements: a low temperature, atmospheric pressure plasma with effective outlet nozzle; an internal cooling system, an end cap, a sensor, an exhaust gas containment system, and a robotic stage that automatically translates the apparatus over the surface area of the wound.

10.0 Method of Treating Wounds

A further embodiment of the present invention is a method of treating wounds that comprises (1) flowing gas containing molecules through a device that converts the molecules into radicals and other reactive species, (2) directing the gas flow, rich in radicals and other reactive species, out of the device and onto the wound, and (3) exposing the wound to the reactive species for a sufficient period of time to cause a therapeutic effect. The therapeutic effect may include killing bacteria, destroying bacterial biofilms, and stimulating regeneration of the damaged tissue.

Gas molecules that are suitable for the invention include but are not limited to oxygen, carbon dioxide, carbon monoxide, nitrogen, nitrous oxide, ammonia and water. These molecules may be converted into ground-state atoms, radicals, ions or metastable molecules that are effective for wound treatment. Oxygen containing gas molecules, such as $O_2$, $CO_2$, and $N_2O$, are particularly well suited for the present invention, because they may be converted into ground-state O atoms, which among other beneficial properties are effective agents for killing bacteria. An advantageous means of generating ground-state atoms and radicals is to feed a mixture of 0.1 to 10.0 volume % of the gas molecules in an inert gas, i.e., helium or argon, to the low-temperature plasma device. The inert gas stabilizes the plasma and maximizes the production of atoms and radicals for the treatment of wounds. For example, a particularly effective wound treatment method would be to feed argon and 0.1 to 10.0 volume % oxygen, carbon dioxide, or nitrous oxide to a low-temperature plasma device, and exposing the wound to the reactive gas species that are generated in the plasma for a time sufficient to provide the therapeutic effect.

An exemplary embodiment of the present invention comprises a method of wound treatment with reactive species contained in flowing gas, wherein a low temperature, atmospheric pressure plasma is used to generate the reactive species. Atmospheric pressure plasmas suitable for the present invention include those that generate a substantially high concentration of ground-state atoms, radicals, ions, or metastable molecules downstream of the plasma generation zone, since the treatment method comprises exposing the wound to said reactive species. Atmospheric pressure plasmas that produce substantially stable molecules, such as nitric oxide or ozone, are not suitable for the present invention.

Another exemplary embodiment of the invention comprises a method of wound treatment with flowing reactive gas species, wherein hot filaments are used to generate the reactive species. When hot filaments are used for this purpose, they must be configured in such a way that a substantially high concentration of ground-state atoms, radicals or metastable molecules flow out of the treatment device and contact the wound.

A further exemplary embodiment of the present invention comprises a method of wound treatment with flowing reactive gas species, wherein a light source is used to generate the reactive species. When a light source, such as an ultraviolet light source, is used for this purpose, the source must be configured in such a way that a substantially high concentration of ground-state atoms, radicals, ions, or metastable molecules flow out of the treatment device and contact the wound.

The method of the present invention comprises a step of directing the gas flow, rich in radicals and other reactive species, out of the device and onto the wound. In this step, it is required that the gas flow velocity is fast enough to prevent the radicals and other reactive gas species from being converted back into stable molecules prior to impinging on the wound. The lifetime of the ground-state atoms, radicals, ions, or metastable molecules in a flow of atmospheric pressure gas is generally less than 50 milliseconds, and in many cases, less than 10.0 milliseconds. Therefore, the outlet of the instrument that generates the reactive gas species should be placed above the wound at a distance of 0.1 to 10.0 cm, and the gas velocity at the outlet should be sufficient that the transit time from the instrument to the wound is less than about 50 milliseconds, and preferably less than 10.0 milliseconds. The means of placing the apparatus above the wound may comprise holding it in the hand, holding it with in a robotic system, mounting it in a fixture that can be positioned over the wound, or mounting it in a fixture that is attached to the patient around the area of the wound. Other means of placing the apparatus may be used without deviating from the scope of the present invention, and would be obvious to those skilled in the art.

The method of the present invention further comprises a step of exposing the wound to the reactive gas species for a sufficient period of time to cause a therapeutic effect, wherein one of the therapeutic effects may be to kill bacteria colonizing the wound. For the purposes of the present invention, a sufficient period of time may be an exposure to the reactive gas for 10.0 seconds to 1.0 hour, and generally in the range of 1.0 minute to 10.0 minutes. Since the wound treatment apparatus may be scanned over the wound, the total treatment time may be longer than the aforementioned time periods. Moreover, it may be advantageous for the patient to be treated with the wound treatment device many times throughout the healing process.

An exemplary embodiment of the present invention is a method of treating infected wounds that comprises (1) flowing gas containing molecules through a device that converts the molecules into radicals and other reactive species, (2) directing the gas flow, rich in radicals and other reactive species, out of the device and onto the wound, and (3) exposing the wound to the reactive species for a sufficient period of time to kill bacteria that have infected the wound. Bacteria that may be effectively killed by the present invention comprise gram-positive bacteria, gram-negative bacteria, obligate aerobes, facultative anaerobes, microaerophilic bacteria, obligate anaerobes, and more specifically, *Streptococcus pyogenes, Staphylococcus aureus, Clostridium perfringens, Pseudomonas aeruginosa, Pseudomonas cepacia, Bacillus anthracis, Streptococcus viridans, Staphylococcus epidermidis, Clostridium tetani, Xanthomonas maltophillia, Bacteroides fragilis, Bacterioides melaminogenicus, Fusobacterium, Yersinia enterocolitica, Francisella tularensis, Pasteurella multocida, Treponema pallidum, Treponema pertenue, Mycobacterium leprae, Salmonella typhi*, and *Serratia*. However, embodiments of the invention are not limited to eliminating these bacteria.

Another exemplary embodiment of the present invention is a method of treating wounds that comprises (1) flowing gas containing molecules through a device that converts the molecules into radicals and other reactive species, (2) directing the reactive gas flow out of the device and onto the wound, (3) exposing the wound to the reactive species for a sufficient period of time to cause a therapeutic effect, and (4) treating the wound with a second therapeutic compound intermittently during the time the wound is exposed to the reactive gas flow. The therapeutic effect may include killing bacteria, destroying bacterial biofilms, and stimulating regeneration of damaged tissue. The second therapeutic compound that is provided to the wound during the treatment process includes but is not limited to saline solution, antimicrobial agents, proteins or enzymes that target specific bacteria and are lethal to them, drugs, proteins or enzymes that stimulate the regeneration of tissue, and drugs, proteins or enzymes that strengthen the immune system of the patient in the effected region.

In the foregoing embodiment of the present invention, many different methods may be used to apply the second therapeutic compound, including but not limited to introducing the compound into a gas that is made to flow over the wound, blotting the wound with a sterile gauze pad that is coated with the compound, spraying the wound with a liquid aerosol containing the compound, applying a solution containing the compound to the wound with a needle and syringe, or using any other practical means of application that would be obvious to those skilled in the art.

11.0 Use of Low Temperature, Atmospheric Pressure Plasmas for Treating Wounds

As previously described, embodiments of the invention may involve use of a low temperature, atmospheric pressure plasma for treating wounds, wherein the plasma generates a substantially high concentration of ground-state atoms, radicals, ions or metastable molecules that flow out of the device and directly contact the wound. Atmospheric pressure plasma devices that are suitable for this embodiment are those that can be held by hand or mounted on a stage and easily manipulated by hand or robot over the wound surface. An exemplary embodiment of the present invention is a low temperature, atmospheric pressure plasma for treating wounds, wherein the plasma is generated by flowing gas into and out of a housing that contains closely spaced electrodes, and by applying radio frequency power to at least one of the electrodes sufficient to breakdown the gas and form a capacitive discharge. Radio frequencies that are suitable for this embodiment of the invention equal n times 13.56 megahertz (MHz), where n is an integer from 1 to 10. A suitable spacing between the electrodes is from 0.2 to 5.0 millimeters, and preferably between 0.5 and 2.0 millimeters, although other spacings could be used and remain within the scope of the present invention.

Another exemplary embodiment of the present invention is the use of a low temperature, atmospheric pressure plasma for treating wounds, wherein the plasma is generated by flowing a mixture of inert gas, such as argon or helium, and a molecular gas, such as oxygen, carbon dioxide, or nitrous oxide, into and out of a housing that contains closely spaced electrodes, and by applying radio frequency power to at least one of the electrodes sufficient to breakdown the gas and form a capacitive discharge. In this embodiment of the present invention, a preferred gas mixture would be helium or argon and between 0.1 and 10.0 volume percent oxygen, and more preferably between 0.5 and 5.0 volume percent oxygen. In another embodiment of this invention, a preferred gas mixture would be helium or argon and between 0.1 and 10.0 volume percent carbon dioxide or nitrous oxide, and more preferably between 0.5 and 5.0 volume percent carbon dioxide or nitrous oxide.

Embodiments of the invention may further involve the use of a low temperature, atmospheric pressure plasma for treating infected wounds, wherein the ground-state atoms, radicals, ions or metastable molecules generated by the plasma directly contact the wound and kill the following microorganisms: gram-positive bacteria, gram-negative bacteria, obligate aerobes, facultative anaerobes, microaerophilic bacteria, obligate anaerobes, and more specifically, *Streptococcus pyogenes, Staphylococcus aureus, Clostridium perfringens, Pseudomonas aeruginosa, Pseudomonas cepacia, Bacillus anthracis, Streptococcus viridans, Staphylococcus epidermidis, Clostridium tetani, Xanthomonas maltophillia, Bacteroides fragilis, Bacterioides melaminogenicus, Fusobacterium, Yersinia enterocolitica, Francisella tularensis, Pasteurella multocida, Treponema pallidum, Treponema pertenue, Mycobacterium leprae, Salmonella typhi*, and *Serratia*. However, embodiments of the invention are not limited to eliminating these microorganisms.

The foregoing description, including the preferred embodiments of the invention, has been presented for the purposes of illustration and description. It is not intended to be exhaustive or to limit the invention to the precise form disclosed. Many modifications and variations are possible in light of the above teaching. The above specification provides a complete description of the apparatus, method and use of the invention.

What is claimed is:

1. An apparatus comprising:
  a plasma generating device for producing a flow of gas comprising at least one reactive gas species in a low temperature, atmospheric pressure plasma;
  a nozzle coupled to the plasma generating device for delivering the at least one reactive gas species to a wound;
  a cooling system including a cooling fluid circulating around the nozzle to cool the flow of the gas; and
  a proximity sensor for providing a feedback signal indicating proximity of the nozzle to the wound;
  wherein the low temperature, atmospheric plasma is generated by applying radio frequency power to at least one of closely spaced electrodes sufficient to breakdown the gas and form a capacitive discharge, the closely spaced electrodes comprising a first surface of a first electrode and a second surface of a second electrode machined into the same shape forming a uniform gap between the surfaces in contact with the gas flow where the low temperature, atmospheric pressure plasma is generated.

2. The apparatus of claim 1, further comprising a gas flow system providing the flow of the gas to the plasma generating device.

3. The apparatus of claim 1, further comprising an electrical power supply coupled to the plasma generating device for generating the at least one reactive gas species.

4. The apparatus of claim 1, wherein the nozzle comprises a shape selected from the group consisting of a disc, a rectangle, a cone, and a hemisphere, wherein the shape has at least one opening for the at last one reactive gas species to flow out.

5. The apparatus of claim 1, wherein the plasma generating device comprises a hand-held device.

6. The apparatus of claim 1, further comprising a robotic arm coupled to the plasma generating device for scanning the at least one reactive gas species over the wound.

7. The apparatus of claim 1, further comprising a control unit coupled to the plasma generating device for supplying a rate and gas composition of the gas flow and electric power to the plasma generating device for generating the at least one reactive gas species.

8. The apparatus of claim 1, further comprising a detachable end cap over the nozzle for protecting the wound from cross-contamination.

9. The apparatus of claim 1, further comprising an exhaust gas system for drawing any potentially harmful gases in the gas flow including the at least one reactive gas species away from a patient with the wound.

10. The apparatus of claim 1, wherein the at least one reactive gas species is selected from the group consisting of oxygen atoms, nitrogen atoms, hydrogen atoms, and hydroxyl radicals.

11. The apparatus of claim 1, wherein the nozzle includes a chemical outlet for delivering a chemical compound to the wound.

12. The apparatus of claim 11, wherein the at least one reactive gas species causes the chemical compound to bond to cells of the wound.

13. A method comprising:
flowing a gas;
generating a low temperature, atmospheric pressure plasma comprising at least one reactive gas species;
delivering the at least one reactive gas species to a wound;
cooling the low temperature, atmospheric pressure plasma so that the gas flow containing the at least one reactive gas species is at a reduced temperature contacting the wound; and
providing a feedback signal indicating proximity of a nozzle for delivering the at least one reactive gas species to the wound;
wherein the low temperature, atmospheric plasma is generated by applying radio frequency power to at least one of closely spaced electrodes sufficient to breakdown the gas and form a capacitive discharge, the closely spaced electrodes comprising a first surface of a first electrode and a second surface of a second electrode machined into the same shape forming a uniform gap between the surfaces in contact with the gas flow where the low temperature, atmospheric pressure plasma is generated.

14. The method of claim 13, wherein the at least one reactive gas species is delivered through an outlet nozzle comprising a shape selected from the group consisting of a disc, a rectangle, a cone, and a hemisphere, wherein each shape has at least one hole or slit for the reactive gas to flow out.

15. The method of claim 13, wherein the at least one reactive gas species is delivered to the wound with a hand-held device.

16. The method of claim 13, further comprising scanning the at least one reactive gas species over the wound with a robotic arm coupled to the plasma generating device.

17. The method of claim 13, further comprising protecting the wound from cross-contamination with a detachable end cap over a nozzle for delivering the at least one reactive gas species to the wound.

18. The method of claim 13, wherein the gas comprises a mixture of gas species, selected from the group consisting of oxygen, carbon dioxide, carbon monoxide, nitrogen, nitrous oxide, ammonia, water, air, helium, and argon.

19. The method of claim 13, wherein the at least one reactive gas species is selected from the group consisting of oxygen, nitrogen, hydrogen, and hydroxyl radicals.

20. The method of claim 13, further comprising delivering a chemical compound to the wound in combination with the at least one reactive gas species.

21. The method of claim 20, wherein the at least one reactive gas species causes the chemical compound to bond to cells of the wound.

22. An apparatus comprising:
means for flowing a gas;
means for generating a low temperature, atmospheric pressure plasma from the flowing gas that contains at least one reactive gas species;
means for delivering the at least one reactive gas species to a wound;
means for cooling the low temperature, atmospheric pressure plasma so that the gas flow containing the at least one reactive gas species is at a reduced temperature contacting the wound; and
means for providing a feedback signal indicating proximity of the nozzle to the wound;
wherein the low temperature, atmospheric plasma is generated by applying radio frequency power to at least one of closely spaced electrodes sufficient to breakdown the gas and form a capacitive discharge, the closely spaced electrodes comprising a first surface of a first electrode and a second surface of a second electrode machined into the same shape forming a uniform gap between the surfaces in contact with the gas flow where the low temperature, atmospheric pressure plasma is generated.

* * * * *